(12) United States Patent
Velasco Valcke

(10) Patent No.: US 11,628,307 B2
(45) Date of Patent: Apr. 18, 2023

(54) DEVICE FOR ELECTRICAL AND MAGNETIC TISSUE STIMULATION

(71) Applicant: PANACEA QUANTUM LEAP TECHNOLOGY LLC, Dallas, TX (US)

(72) Inventor: Francisco Javier Velasco Valcke, Bogotá (CO)

(73) Assignee: PANACEA QUANTUM LEAP TECHNOLOGY LLC, Dallas, TX (US)

( * ) Notice: Subject to any disclaimer, the term of this patent is extended or adjusted under 35 U.S.C. 154(b) by 203 days.

(21) Appl. No.: 16/764,530

(22) PCT Filed: Nov. 17, 2018

(86) PCT No.: PCT/IB2018/059075
§ 371 (c)(1),
(2) Date: May 15, 2020

(87) PCT Pub. No.: WO2019/097488
PCT Pub. Date: May 23, 2019

(65) Prior Publication Data
US 2020/0368545 A1    Nov. 26, 2020

(30) Foreign Application Priority Data

Nov. 17, 2017    (CO) .................... NC2017/0011756

(51) Int. Cl.
*A61N 2/00*        (2006.01)
*A61N 1/04*        (2006.01)
(52) U.S. Cl.
CPC ........... *A61N 2/002* (2013.01); *A61N 1/0428* (2013.01); *A61N 1/0468* (2013.01)

(58) Field of Classification Search
CPC .... A61N 2/002; A61N 1/0428; A61N 1/0468; A61N 1/0456; A61N 1/3603
See application file for complete search history.

(56) References Cited

U.S. PATENT DOCUMENTS 5,658,322 A    8/1997  Fleming
5,718,662 A    2/1998  Jalinous
(Continued)

FOREIGN PATENT DOCUMENTS

| CA | 2801333 A1 | 12/2011 |
| CA | 2977584 A1 | 9/2016 |
| EP | 1578266 B1 | 4/2015 |

OTHER PUBLICATIONS

International Search Report dated Mar. 12, 2019 for PCT/IB2018/059075.

(Continued)

*Primary Examiner* — Mallika D Fairchild
(74) *Attorney, Agent, or Firm* — Fountainhead Law Group P.C.

(57) ABSTRACT

This invention corresponds to an electrical and magnetic tissue stimulation device comprising a multi-source distribution circuit, a decoupled output stage circuit connected to the multi-source distribution circuit and to a control unit; the control unit is connected to the multi-source distribution circuit and to the decoupled output stage circuit, where the control unit generates PE and Out outputs for electrical and magnetic stimulation of a tissue.

The invention also has a multi-source distribution circuit that comprises a control unit connected to a source output selector. A voltage regulator circuit is connected to a current limiter. The current limiter is connected to a capacitor, to a capacitor bank and to the source output sector, wherein the control unit controls the source output selector by means of (Continued)

an output control signal bus, the source output selector connects or disconnects one or more capacitors from the capacitor bank.

20 Claims, 17 Drawing Sheets

(56) References Cited

U.S. PATENT DOCUMENTS 9,572,978 B2 2/2017 Bernhard et al.
2013/0090712 A1* 4/2013 Popovic ............... A61N 1/0476
607/148

OTHER PUBLICATIONS

Written Opinion of the International Searching Authority dated Mar. 12, 2019 for PCT/IB2018/059075.

* cited by examiner

DEVICE FOR ELECTRICAL AND MAGNETIC TISSUE STIMULATION

CROSS REFERENCE TO RELATED APPLICATIONS

This application is the National Stage of International Application No. PCT/IB2018/059075, filed Nov. 17, 2018, and claims benefit of Columbian Patent Application No. NC2017/0011756 filed on Nov. 17, 2017.

FIELD OF THE INVENTION

This invention is related to an electrical and magnetic tissue stimulation device. The device includes a multi-source distribution circuit. Electrodes for electric stimulation are connected, as well as transducers for magnetic stimulation or different types of stimulation (e.g. Peltier cells for cold stimulation, heat generators, vibration motors, coils for inductive stimulation or a combination thereof.

BACKGROUND OF THE INVENTION

A number of devices used for procedures and therapies have been used so far in relation with the healing of wounds, disease treatment, cell stimulation, osteogenesis, dielectrophoresis, transcutaneous electrical nerve stimulation, and generation of bioactive frequencies, which are frequencies with a biological activity within the human body, thus bringing benefits to health, chemotherapy treatments, among others. The application of various types of stimulation and/or drugs help with body's natural healing functions.

Existing electrical, magnetic, capacitive, inductive, thermal, or vibration stimulation devices or a combination thereof comprise a stimulation unit coupled for at least one transducer. Transducers are adapted to administer the stimulation treatment of a user's tissue, and the stimulation unit provides a given number of pulses, which are applied at a determined frequency, amplitude, and pulse width.

For correct electrical, magnetic, capacitive, inductive, thermal, or vibration stimulation or a combination thereof in which the frequency, amplitude, and pulse width of the pulse train vary, regarding the stimulation generator, the power supply is required to be adaptable to different settings, stimulation treatment intensities, and other physical, electrical, magnetic, thermal, motion, capacitive, inductive features or a combination thereof defined by the impedance of the tissue to be stimulated.

The state of the art discloses devices for electrical or magnetic tissue stimulation, such as, for example, those disclosed in documents U.S. Pat. Nos. 5,718,662 and 5,658,322.

Document U.S. Pat. No. 5,718,662 discloses a stimulator for neuro-muscular tissues having a stimulating coil which is energized by discharging capacitors at different times. The discharging capacitors bank is connected to a discharging circuits bank, which vary the amplitude and/or frequency of a stimulation pulse train, for the tissue to be treated.

Document. U.S. Pat. No. 5,658,322 discloses a system and method for generating bioactive frequencies, comprising a generator of specific frequencies, which is controlled by a programmable control unit. The programmable control unit generates a specific frequency or a series of specific frequencies from the frequency generator. The invention discloses a capacitors bank with constant capacitance value, which allows for the filtration of the external source. Also, a user, using a keyboard, selects a specific frequency, a sequence of specific frequencies or a series of programmed frequencies in the control unit.

Based on the foregoing, it may be seen that device disclosed by document U.S. Pat. No. 5,718,662, for electrical or magnetic stimulation of neuro-muscular tissues is unable to read the behavior of the treated tissue, i.e. the impedance value of the tissue treated is not feedback. Due to the lack of feedback, it is not possible to know the process of the treatment necessary for each user. Therefore, close monitoring by physicians or trained personnel for the correct use of the device is required.

In turn, the lack of feedback of the tissue impedance value allows for muscular overstimulation, which causes fatigue in the treated muscle, thus causing damage to a muscle. Simultaneously, the device does not allow to monitor the patient's treatment in terms of duration or minimum levels of muscle effort.

Moreover, device disclosed in document U.S. Pat. No. 5,658,322 does not allow for automatic setting of amplitude, frequency and pulse width, for the tissue properties in conditions to ensure the proper treatment protocol and security enhancement. Since the value of the external cannot be changed, it is not possible to adjust the external source in different settings.

Therefore, the state of the art discloses devices for electrical or magnetic stimulation of tissues. However, these devices do not allow for automatic setting of the type of stimulation and proper treatment for the tissue to be treated.

In addition, variations in the value of source are not allowed, thus, different settings for treatment are not enabled, i.e. in case of changes in impedance of the treated tissue, devices are unable to operate.

BRIEF DESCRIPTION OF THE INVENTION

This invention is related to an electrical and magnetic tissue stimulation device comprising a multi-source distribution circuit (3), a decoupled output stage circuit (4) connected to the multi-source distribution circuit (3) and to a control unit; the control unit (1) is connected to the multi-source distribution circuit (3) and to the decoupled output stage circuit (4), wherein the control unit (1) generates PE (12) and Out (13) outputs for electrical and magnetic stimulation of a tissue.

DETAILED DESCRIPTION OF THE INVENTION

Figure 1:
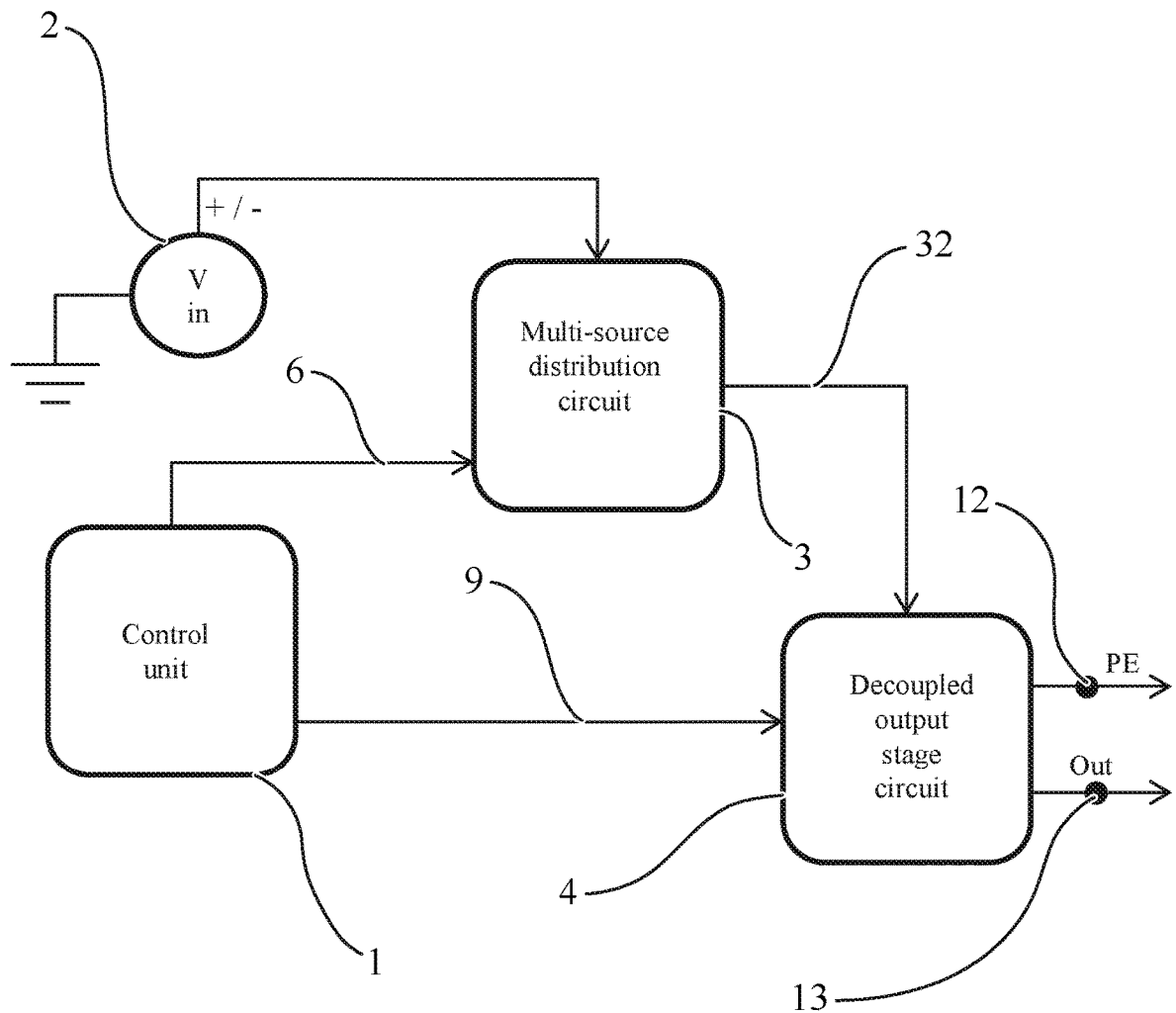
FIG. 1 shows an invention diagram comprising a multi-source distribution circuit (3) connected to an external source (2), to a control unit (1) and to a decoupled output stage circuit (4).

Referring to FIG. 1, there is an external source (2) that allows DC or AC power. A multi-source distribution circuit (3) is connected to the external source (2) and to a control unit (1). The purpose of the control unit (1) consists of selecting the multi-source distribution (see explanation below) and of managing stimulation signals (9) targeted to a decoupled output stage circuit (4), either with electrical or magnetic stimulation for the spot to be stimulated.

The decoupled output stage circuit (4) is connected in turn to the multi-source distribution circuit (3) and to the control unit (1). The control unit (1) sends stimulation signals (9). The decoupled output stage circuit (4) has two outputs, PE (12) and Out (13). A transducer is connected to PE (12) and Out (13) outputs. In order to understand this invention, transducer, actuator, motors, electrodes, photo-electrical items, induction actuators, heat generators, resistors, coils are understood to generate magnetic fields by induction, Peltier cells, antennas, or combinations thereof.

There are different types of stimulation, such as those made up by the group of electrical, magnetic, capacitive, inductive, thermal, vibrational, or photo-electrical stimulation, or a combination thereof.

Figure 2:
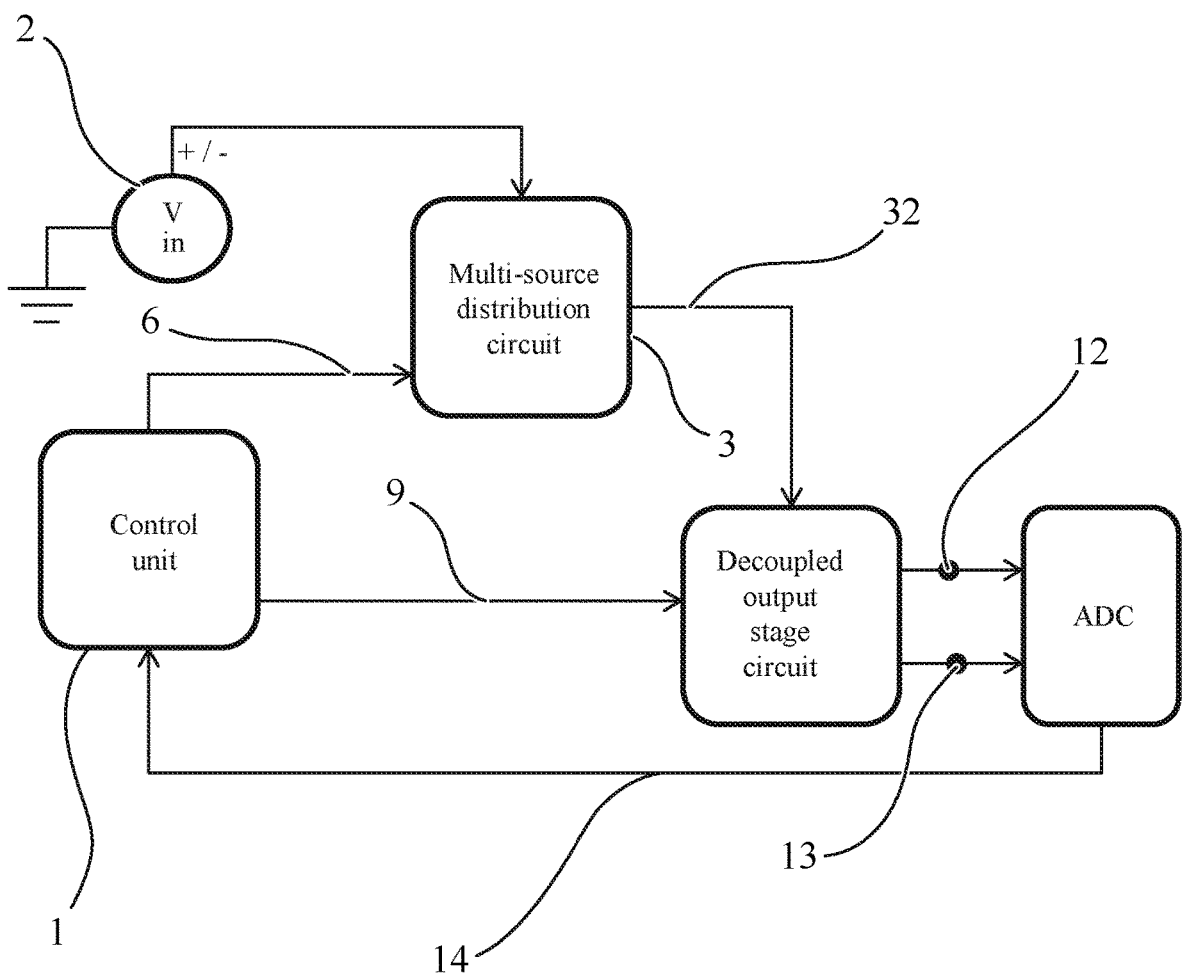
FIG. 2 shows an invention diagram where an analogue-to-digital converter [ADC] (5) is connected to the decoupled output stage circuit (4), which enables feedback to the control unit (1).

In an embodiment of the invention, and referring to FIG. 2, there is an external source (2) connected to the multi-source distribution circuit (3). The multi-source distribution circuit (3) is in turn connected to a control unit (1) and to the decoupled output stage circuit (4).

The decoupled output stage circuit (4) is connected through PE (12) and Out (13) outputs to an analogue-to-digital converter [ADC] (5), which sends the digitalized signal (9) from PE (12) and Out (13) channel to the control unit (1). The control unit (1) through the variations existing in PE (12) and Out (13) makes decisions to feedback the decoupled output stage circuit (4) with different stimulation signals (9). Typically, these variations depend on the variation in the load of electrodes by each one of PE (12) and Out (13) channels.

That is, when a tissue is connected at these spots, the impedance of the stimulated tissue changes, and by changing its impedance through the analogue-to-digital converter [ADC] (5), variations of current and voltage are monitored. With these variations of current and voltage, changes in connected impedance are monitored. Depending upon the change in impedance, the control unit (1) changes the electrical stimulation signal (9).

This form of decoupled output stage circuit (4) makes a different stimulation to the concerning tissue. For the case of FIG. 2, the multi-source distribution circuit has a v. Out (32) output. The external source (2) of stimulation is either positive or negative.

Figure 3:
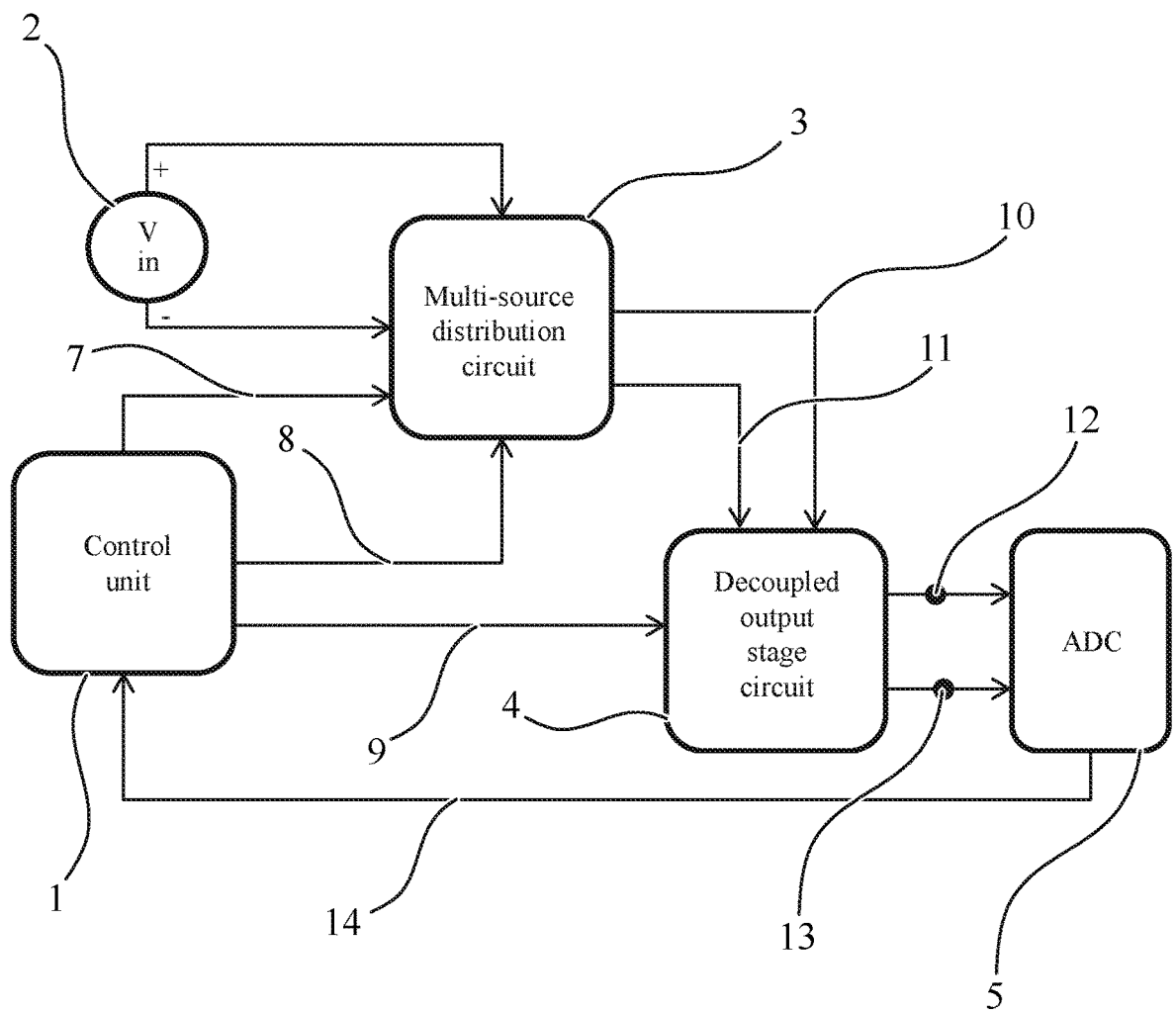
FIG. 3 shows an invention diagram where the external source (2) is a dual source, in an embodiment of the invention.

Referring to FIG. 3, the external source (2) is a positive/negative source, i.e. a dual source, connected to the multi-source distribution circuit (3). The multi-source distribution circuit (3) is connected to the control unit (1), which selects outputs for the multi-source distribution circuit (3). In this manner, multi-source distribution circuit (3) enables positive v. Out (10), negative v. Out (11), positive output and negative output, in both quadrants, dual or taking the entire range between positive and negative, with zero crossing, i.e. there are signals at zero.

The multi-source distribution circuit (3) is connected to the decoupled output stage circuit (4), through positive v. Out (10), negative v. Out (11) outputs, to carry out stimulation to the desired tissue. The decoupled output stage circuit (4) is connected to an analogue-to-digital converter [ADC] (5) to provide feedback (14) to the control unit (1).

Figure 4:
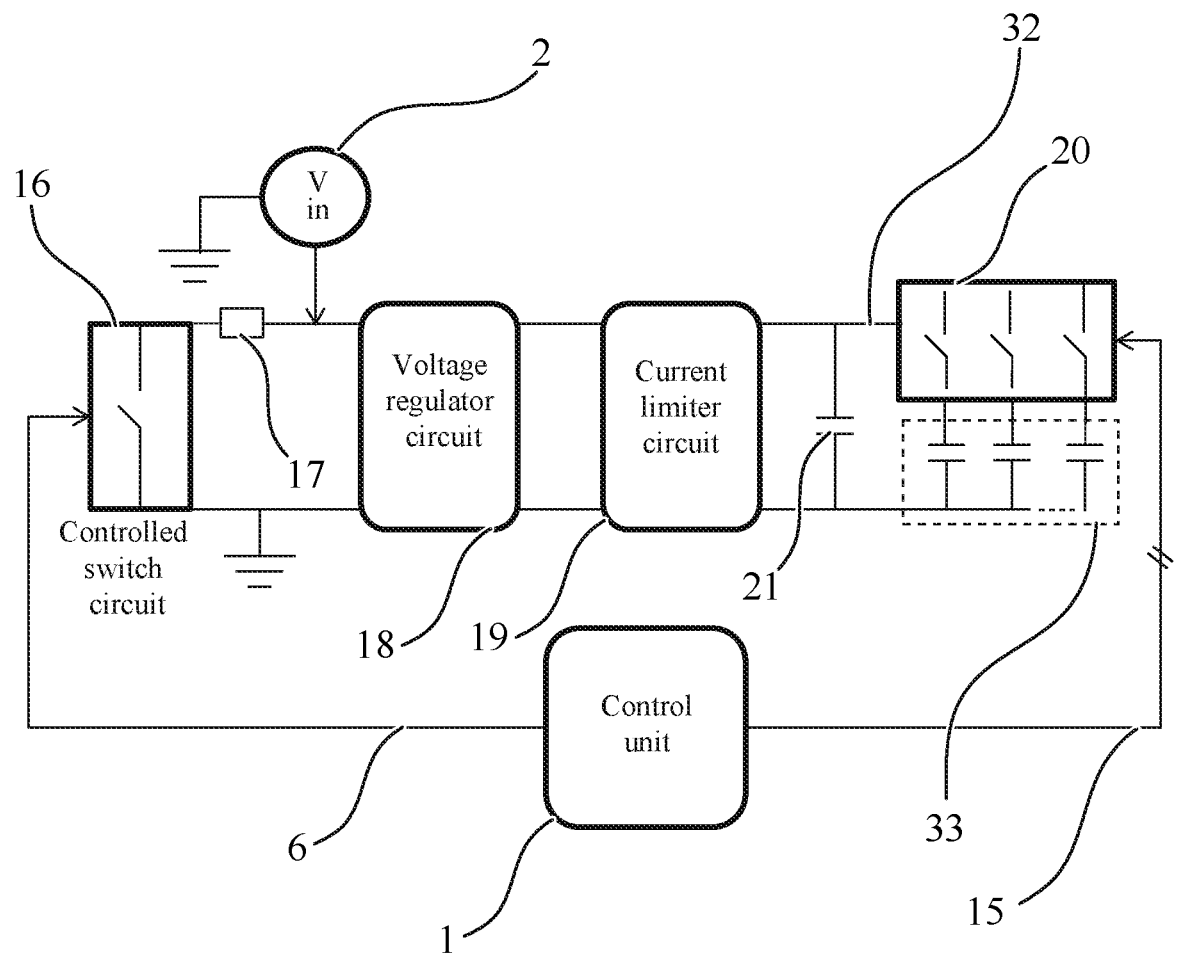
FIG. 4 shows a diagram for the multi-source distribution circuit (3), comprising a control unit (1) connected to a controlled switch circuit (16) and to a source output selector (20), in an embodiment of the invention. The controlled switch circuit (16) is connected to a voltage regulator circuit (18), which is connected to a current limiter (19).

In an embodiment of the invention, and referring to FIG. 4, the multi-source distribution circuit (3) consists of a controlled switch circuit (16) commanded by the control unit (1), through a source control line (6). The controlled switch circuit (16) has an impedance (17) that helps to prevent a short circuit when the controlled switch circuit (16) is closed.

The controlled switch circuit (16) is connected to a voltage regulator (18) and the external source (2). The voltage regulator circuit (18) is selected by the control unit (1) when the controlled switch circuit (16) is closed. In this way, the external source (2) is selected as input. The voltage regulator circuit (18) regulates the external source (2) located at input. A current limiter circuit (19) is connected to the output of the voltage regulator circuit (18). The current limiter circuit (19) keeps the current flow and voltage constant, regardless of impedance changes within a range, and delivers the signal to a output Cp capacitor. (21).

At the end, the output Cp capacitor (21) is connected to a capacitor bank (33) in parallel. The capacitor bank (33) allows to have capacitors of the same capacity or capacitors of different capacity. Capacitors of the capacitor bank (33) are switched through a source output selector (20), commanded by the control unit (1) through an output control line (15). The capacitor bank (33) has "n" capacitors connected in parallel from a natural "n" number greater than zero from a $C_1$ capacitor to a $C_n$ capacitor. Outputs of the source output selector (20) activate or inactivate each capacitor of the capacitor bank (33).

Figure 7:
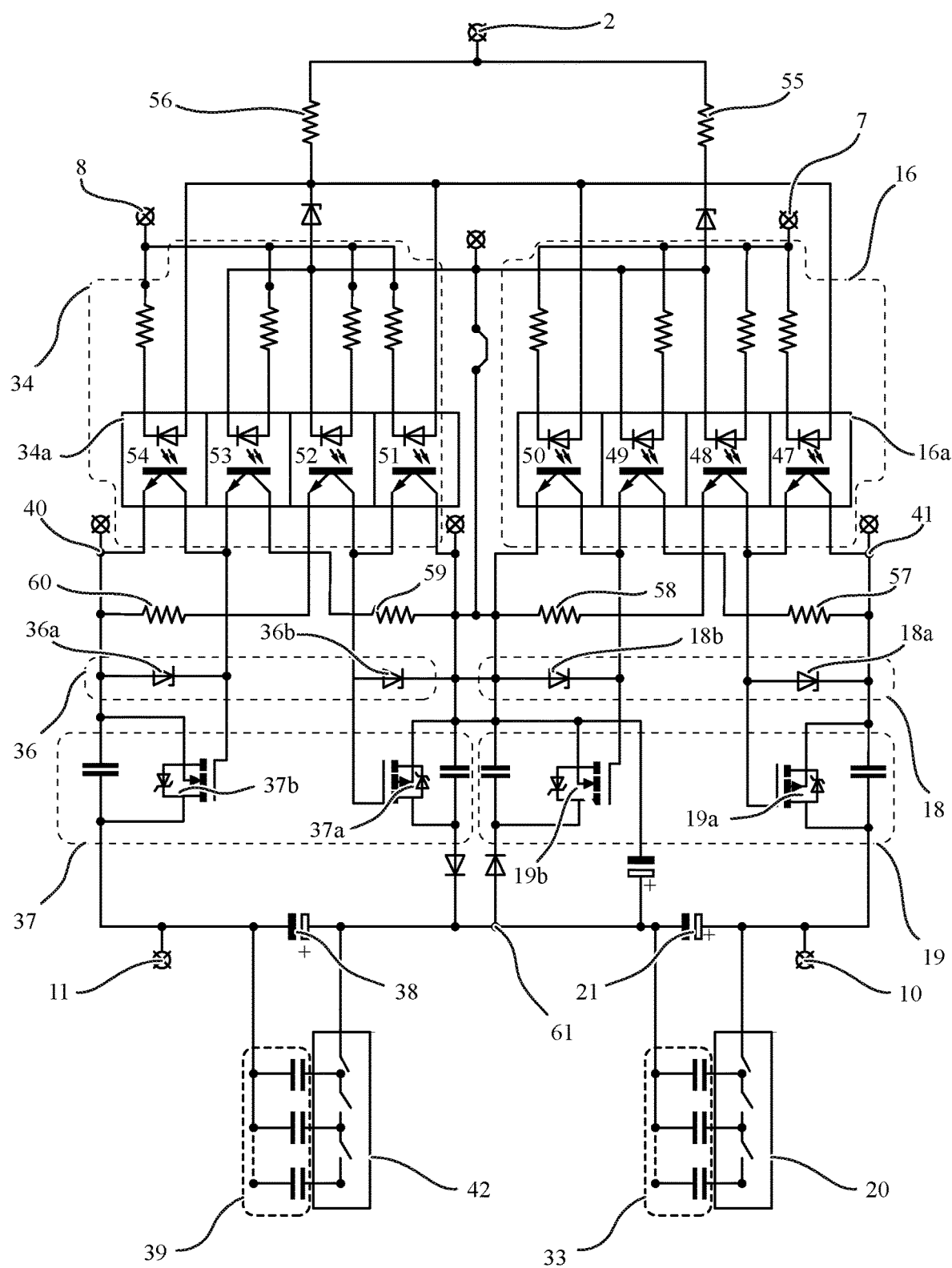
FIG. 7 shows the multi-source distribution circuit (3) used in this invention, in an embodiment of the invention.

Referring to FIG. 4 and FIG. 7, in an embodiment of the present invention, the controlled switch circuit (16) consists of:
- an integrated circuit with optocoupler (16a) with first optocoupler (47), second optocoupler (48), third optocoupler (49), and forth optocoupler (50);
- the anode of the first optocoupler (47) and the anode of the fourth optocoupler (50) are connected;
- the cathode of the second optocoupler (48) and the cathode of the third optocoupler (49) are connected;
- the cathode of the first optocoupler (47) connected to one terminal of resistive impedance, the other terminal of said resistive impedance connected to the high source control signal (7);
- the cathode of the forth optocoupler (50) connected to one terminal of resistive impedance, the other terminal of said resistive impedance connected to the high source control signal (7);
- the anode of the second optocoupler (48) connected to one terminal of resistive impedance, the other terminal of said resistive impedance connected to the high source control signal (7);
- the anode of the third optocoupler (49) connected to one terminal of resistive impedance, the other terminal of said resistive impedance connected to the high source control signal (7);
- the emitter of the first optocoupler (47) connected to the collector of the second optocoupler (48);
- the emitter of the third optocoupler (49) connected to the collector of the fourth optocoupler (50);
- the collector of the first optocoupler (47) connected with a first high protection impedance (57), the other terminal of said high protection impedance (57) connected to the collector of the third optocoupler (49);
- the emitter of the second optocoupler (48) connected to a second high protection impedance (58).

Referring to FIG. 4, the controlled switch circuit (16) is selected from the group formed by relay circuits, optocouplers, controlled selectors, breakers, transistors, or combinations thereof.

The voltage regulator circuit (18) is selected from the grouped formed by integrated circuits, Zener diodes, circuit with capacitors, circuits with coils, circuits with transistors, electromechanical regulators, or combinations thereof.

The current limiter circuit (19) is selected from the grouped formed by integrated circuits, circuits with diodes, circuits with transistors, circuits with capacitors and resistors, circuits with coils and resistors, or combinations thereof.

In a non-illustrated embodiment of this invention, the capacitor bank (33) is connected at the end that is not connected to a source output selector (20), a second source output selector that allows connecting in series and/or in parallel each one of the capacitors of the capacitor bank (33).

The output control (15) which is commanded by the control unit (1), switches the capacitors of the capacitor bank (33), which are connected in parallel with the output capacitor Cp (21). The output capacitor Cp. (21) is connected to the current limiting circuit (19). The equivalent capacitor between the capacitor bank (33) and the output capacitor Cp (21) is connected to the V. Out output (32). When a capacitor in the capacitor bank (33) that is in parallel with the output capacitor Cp (21) is switched, the amount of output load changes.

Figure 5:
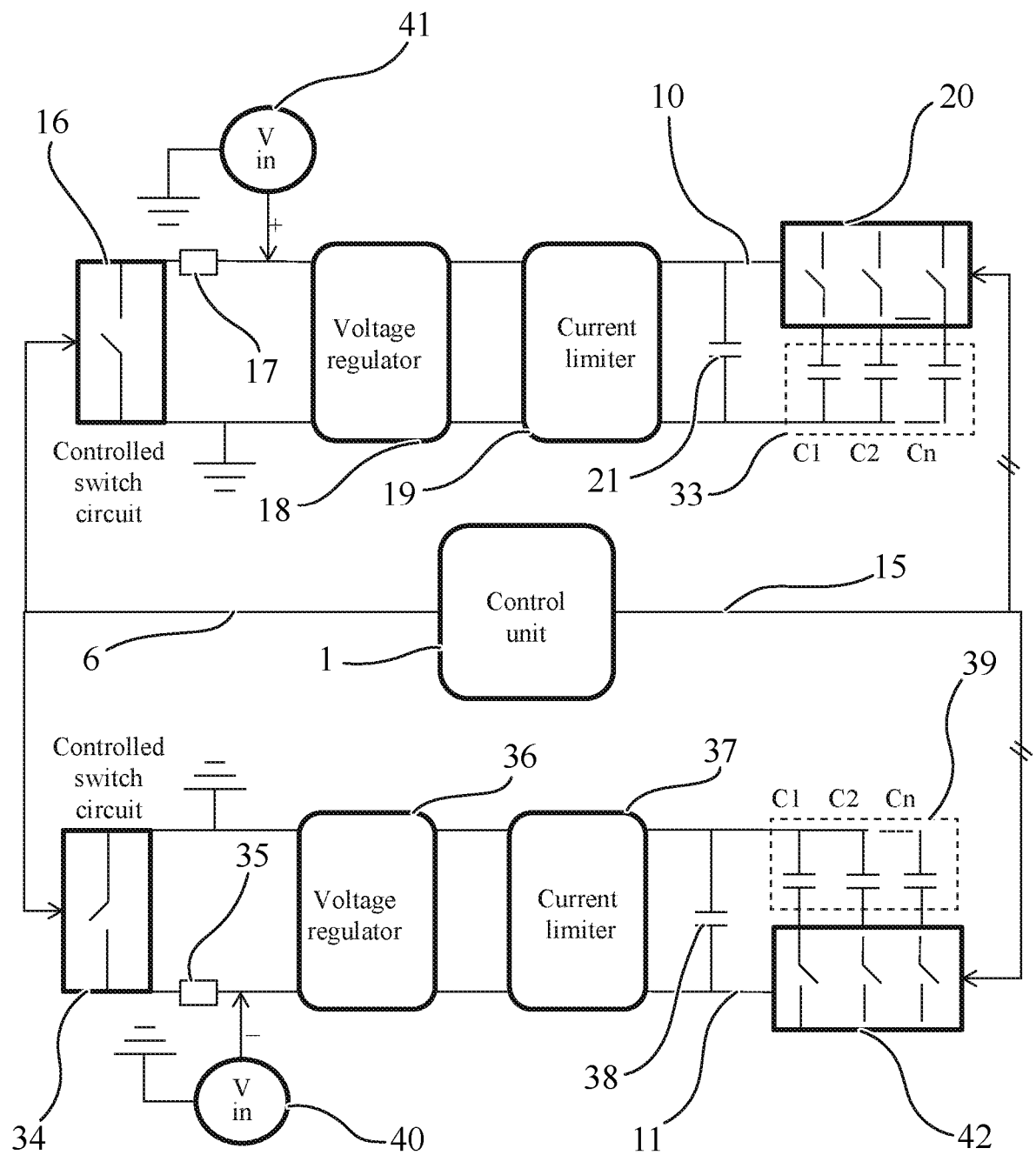
FIG. 5 shows a diagram for the multi-source distribution circuit (3) where the external source (2) is a dual source, i.e. it bears positive and negative values, in an embodiment of the invention.

In an embodiment of the invention and referring to FIG. 5, the multi-source distributor circuit (3) works for both positive sources (41) and negative sources (40). In this way, a control unit (1) is connected to a controlled switch circuit (16) through a source control line (6). The controlled switch circuit (16) is connected to an impedance (17) that helps prevent a short circuit when the controlled switch circuit (16) is closed.

The controlled switch circuit (16) is connected to a voltage regulator (18) and the positive external source (41). The voltage regulator circuit (18) is selected by the control unit (1) when the controlled switch circuit (16) is closed, in this way, the external source (41) is selected as input. The voltage regulator circuit (18) regulates the external source (41) selected as input. A current limiter circuit (19) is connected to the output of the voltage regulator circuit (18). The current limiter circuit (19) keeps the current flow and voltage constant, regardless of impedance changes within a range, and delivers the signal to a output Cp capacitor. (21).

At the end, the output Cp capacitor (21) is connected to a capacitor bank (33) in parallel. Capacitors of the capacitor bank (33) are commuted through a source output selector (20), regulated by the control unit (1) through an output control line (15).

The output control (15) that is commanded by the control unit (1) switches the capacitors that are in parallel of the capacitor bank (33) with the output Cp capacitor (21), which is connected to the current limiter circuit (19). The equivalent capacitor between the capacitor bank (33) and the output capacitor Cp (21) is connected to the positive V. Out (10) output. When connecting at least one capacitor in the capacitor bank (33) that are in parallel with the output Cp capacitor (21), the amount of output load changes.

In turn, the control unit (1) is connected to a controlled switch circuit (34) through a source control line (6). The controlled switch circuit (34) is connected to an impedance (35) that helps prevent a short circuit when the controlled switch circuit (34) is closed. The controlled switch circuit (34) is connected to a voltage regulator (36) and the negative external source (40).

The voltage regulator circuit (36) is selected by the control unit (1) when the controlled switch circuit (34) is closed, in this way, the negative source (40) is selected as input. The voltage regulator circuit (36) regulates the negative external source (40) selected as input. A current limiter circuit (37) is connected to the output of the voltage regulator (36) circuit. The current limiter circuit (37) keeps the current flow and voltage constant, regardless of impedance changes within a range, and delivers the signal to a output Cp capacitor (38).

At the end, the output Cp capacitor (38) is connected to a capacitor bank (39) in parallel. Capacitors of the capacitor bank (39) are switched through a source output selector (42), commanded by the control unit (1) through an output control line (15).

The capacitor bank (39) has "n" capacitors connected in parallel from a natural "n" number greater than zero from a $C_1$ capacitor to a $C_n$ capacitor; the outputs of the second source output selector (42) activate or inactivate each capacitor of the capacitor bank (39).

In a non-illustrated embodiment of this invention, the capacitor bank (39) is connected at the end that is not connected to a source output selector (42), a second source output selector that allows connecting in series and/or in parallel each one of the capacitors of the capacitor bank (39).

The output control (15) that is commanded by the control unit (1) switches the capacitors that are in parallel of the capacitor bank (39) with the output Cp capacitor (38), which is connected to the current limiter circuit (37). The equivalent capacitor between the capacitor bank (39) and the output capacitor Cp (38) are connected to the negative V. Out (11) output. When connecting at least one capacitor in the capacitor bank (39) that are in parallel with the output Cp capacitor (38), the amount of output load changes.

Figure 6:
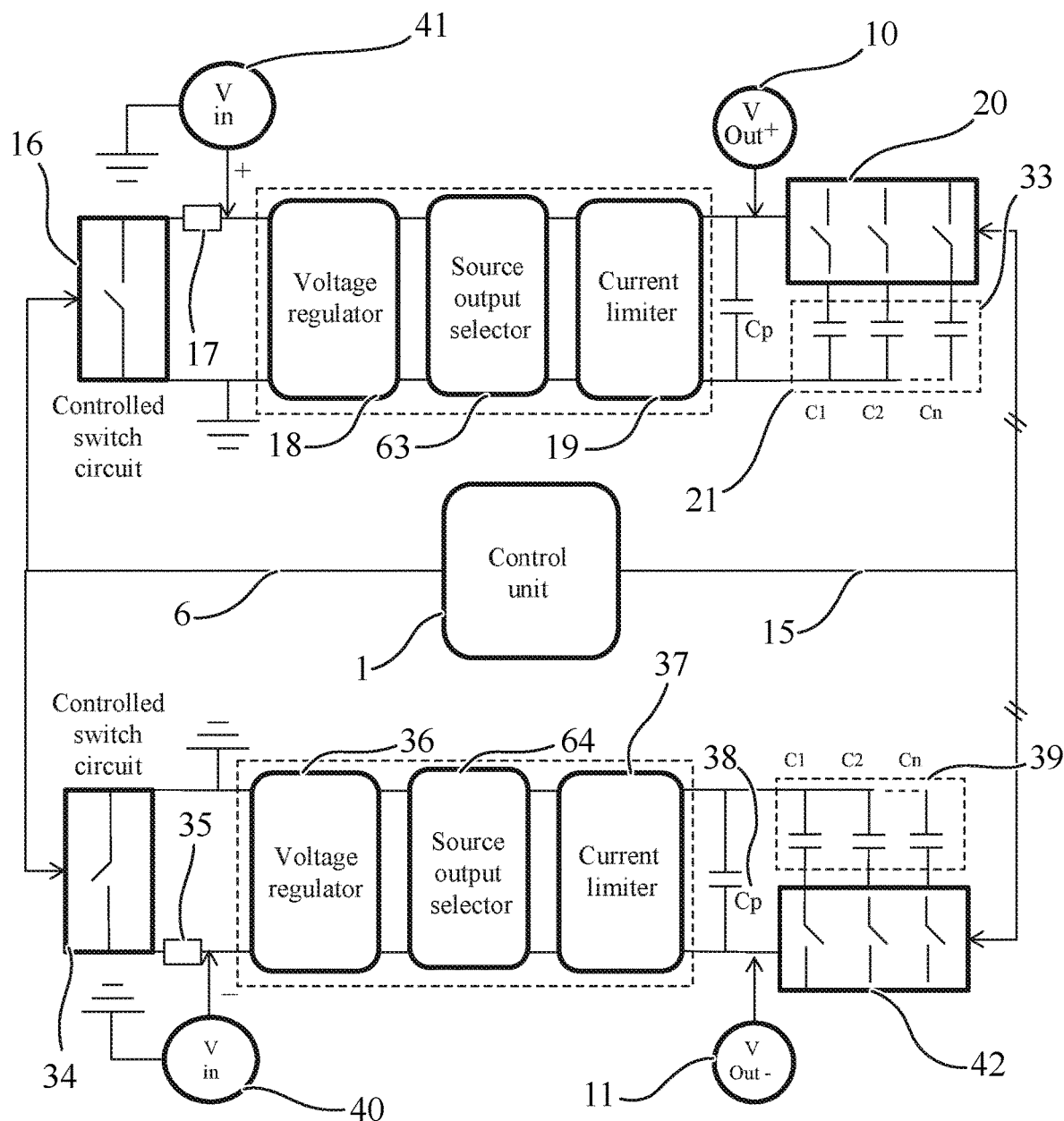
FIG. 6 shows a diagram for the multi-source distribution circuit (3) as having a dual switched source, in an embodiment of the invention.

In an embodiment of the invention and referring to FIG. 6, the multi-source distributor circuit (3) works for both positive sources (41) and negative sources (40).

In this way, a control unit (1) is connected to a controlled switch circuit (16) through a source control line (6). The controlled switch circuit (16) has an impedance (17) that helps to prevent a short circuit when the controlled switch circuit (16) is closed. The controlled switch circuit (16) is connected to a voltage regulator (18) and the external positive source (41). The voltage regulator circuit (18) is selected by the control unit (1) when the controlled switch circuit (16) is closed, in this way, the external source (41) is selected as input. The voltage regulator circuit (18) regulates the external source (41) selected as input.

At the output of the voltage regulator circuit (18), a source output selector 63 is connected, the function of the source output selector (63) is to convert the positive external source (41) to a switched source, this allows greater stability in current and voltage. A current limiter circuit (19) is connected to the output of the source output selector 63. The current limiter circuit (19) keeps the current flow and voltage constant, regardless of impedance changes within a range, and delivers the signal to a output Cp capacitor (21).

At the end, the output Cp capacitor (21) is connected to a capacitor bank (33) in parallel. Capacitors of the capacitor bank (33) are switched through a source output selector (20), commanded by the control unit (1) through an output control line (15). The output control (15) that is commanded by the control unit (1) connects at least one capacitor in parallel to the capacitor bank (33) with the output Cp capacitor (21), which is connected to the current limiter circuit (19). The equivalent capacitor between the capacitor bank (33) and the output capacitor Cp (21) is connected to the positive V. Out (10) output. When connecting at least one capacitor in the capacitor bank (33) that are in parallel with the output Cp capacitor (21), the amount of output load changes.

In turn, the control unit (1) is connected to a controlled switch circuit (34) through a source control line (6). The controlled switch circuit (34) is connected to an impedance (35) that helps prevent a short circuit when the controlled switch circuit (34) is closed. The controlled switch circuit (34) is connected to a voltage regulator (36) and the negative external source (40). The voltage regulator (36) circuit is selected by the control unit (1) when the controlled switch circuit (34) is closed. In this way, the negative source (40) is selected as input. The voltage regulator circuit (36) regulates the external source (40) selected as input.

At the output of the voltage regulator circuit (18), a source output selector 64 is connected, the function of the source output selector 64 is to convert the negative external source (40) to a switched source, this allows greater stability in current and voltage. At the output of the source output selector 64. A current limiter circuit (37) is connected to the output of the source output selector (36). The current limiter circuit (37) keeps the current flow and voltage constant, regardless of impedance changes within a range, and delivers the signal to a output Cp capacitor (38).

The output control (15) that is commanded by the control unit (1) connects at least one capacitor in parallel to the capacitor bank (39) with the output Cp capacitor (38), which is connected to the current limiter circuit (37). The equivalent capacitor between the capacitor bank (39) and the output capacitor Cp (38) are connected to the output negative V. Out (11). When switching at least one capacitor in the capacitor bank (39) that are in parallel with the output Cp capacitor (38), the amount of output load changes.

In an embodiment of the invention, and referring to FIG. 7, there is a circuit for the multi-source distribution circuit (3). The circuit has an external source (2), which can be, for example, 5 volts, a positive external source (41) and a negative external source (40).

The controlled switch circuit (16) consists of four optocouplers, which are connected in pairs in parallel, to switch the positive external source (41). The external source (2) is connected to a resistive impedance (55). The resistive impedance (55) is connected to the input of two optocouplers, specifically optocouplers (47) and (50). At the input of the other pair of optocouplers, specifically (48) and (49), the high source control signal (7) is connected. Each of the optocouplers is duly protected by a limiting impedance.

When the control unit (1) sends a control signal, through a high source control line (7), a pair of optocouplers starts to conduct; when this signal is changed, the other pair starts to conduct. Each of the optocouplers has an input to impedance that has the function of limiting the current for the LED diode of each optocoupler.

To prevent a short circuit when the control unit (1) sends a signal (9), through a high source control line (7), so as not to select the positive external source (41), two resistive impedances (57) and (58) are connected.

At the output of the controlled switch circuit (16), a voltage regulator circuit (18) is connected. The voltage regulator circuit (18) consists of two Zener diodes. The Zener diode (18a) is connected in parallel with the optocoupler (47) and in series with the optocoupler (48) and the Zener diode (18b) is connected in parallel with the optocoupler (50) and in series with the optocoupler (49). A current limiter circuit (19) is connected to the output of the voltage regulator circuit (18). Each of the optocouplers is duly protected by a limiting impedance.

The current limiting circuit (19) consists of two MOSFET transistors. MOSFET transistors have their own protection diode. The p-channel MOSFET transistor (19a) is connected to the positive external source (41) through the Source pin. The transistor (19a) is connected to the positive V. Out (10) output and to the output Cp capacitor (21), through the Drain pin. At the transistor Gate pin (19a), the optocouplers (47) and (48) are simultaneously connected.

The n-channel MOSFET transistor (19b) is connected through its Drain and Source pins, to the circuit reference, i.e. GND. In turn, the Gate pin of the transistor (19b) is simultaneously connected to the optocouplers (49) and (50); and in turn, to the Source pin, a decoupling capacitor (C4) is connected, which allows the input source and the output impedance to be decoupled. Transistors (19a) and (19b) keep the current constant, despite changes in impedance. The current limiter circuit (19) is connected to an output Cp capacitor (21).

The output Cp capacitor (21) is connected in parallel to a capacitor bank (33). In addition, a decoupling capacitor is connected to the output Cp capacitor (21). To connect at least one capacitor from the capacitor bank (33), the control unit (1) sends a signal (9) and switches the source output selector (20). The source output selector (20) connects at least one capacitor from the capacitor bank (33) in parallel with the output Cp capacitor (21), which is in turn connected to the positive V. Out (10) output.

The parallel between the output Cp capacitor (21) and at least one of the capacitors from the capacitor bank (33) allows to vary the output load.

The controlled switch circuit (34) consists of four optocouplers, which are connected in pairs in parallel, to switch the negative external source (40). The 5-volt external source (2) is connected to a resistive impedance (56). The resistive impedance (56) is connected to the input of two optocouplers, specifically optocouplers (51) and (54). At the input of the other pair of optocouplers, specifically (52) and (53), the low source control signal (8) is connected.

When the control unit (1) sends a control signal, through a low source control line (8), a pair of optocouplers starts to conduct; when this signal changes, the other pair of optocouplers starts to conduct. Each of the optocouplers has an input to impedance that has the function of limiting the current for the LED diode of each optocoupler.

To prevent a short circuit when the control unit (1) sends a signal (9), through a low source control line (8), so as not to select the negative external source (40), two resistive impedances (59) and (60) are connected.

At the output of the controlled switch circuit (34), a voltage regulator circuit (36) is connected. The voltage regulator circuit (36) consists of two Zener diodes. The Zener diode (36b) is connected in parallel with the optocoupler (51) and in series with the optocoupler (52) and the Zener diode (36a) is connected in parallel with the optocoupler (54) and in series with the optocoupler (53). A current limiter circuit (37) is connected to the output of the voltage regulator circuit (36).

The current limiting circuit (37) consists of two MOSFET transistors. MOSFET transistors have their own protection diode. The n-channel MOSFET transistor (37b) is connected to the negative external source (40) through the Source pin. The transistor (37b) is connected to the negative V. Out (11) output and to the output Cp capacitor (38), through the Drain pin. At the transistor Gate pin (37b), the optocouplers (53) and (54) are simultaneously connected.

The p-channel MOSFET transistor (37a) is connected through its Drain and Source pins to the circuit reference, i.e. GND. In turn, the transistor Gate pin (37a) is simultaneously connected to the optocouplers (51) and (52). Transistors (37a) and (37b) keep the current constant, despite changes in impedance. The current limiter circuit (37) is connected to an output Cp capacitor (38).

The output Cp capacitor (38) is connected in parallel to a capacitor bank (42). To connect at least one capacitor from the capacitor bank (42), the control unit (1) sends a signal (9) and switches the source output selector (39). The source output selector (39) connects at least one capacitor from the capacitor bank (42) in parallel with the output Cp capacitor (38), which is in turn connected to the negative V. Out (11) output.

The parallel between the output Cp capacitor (38) and at least one of the capacitors from the capacitor bank (39) allows to vary the output load.

Figure 8:
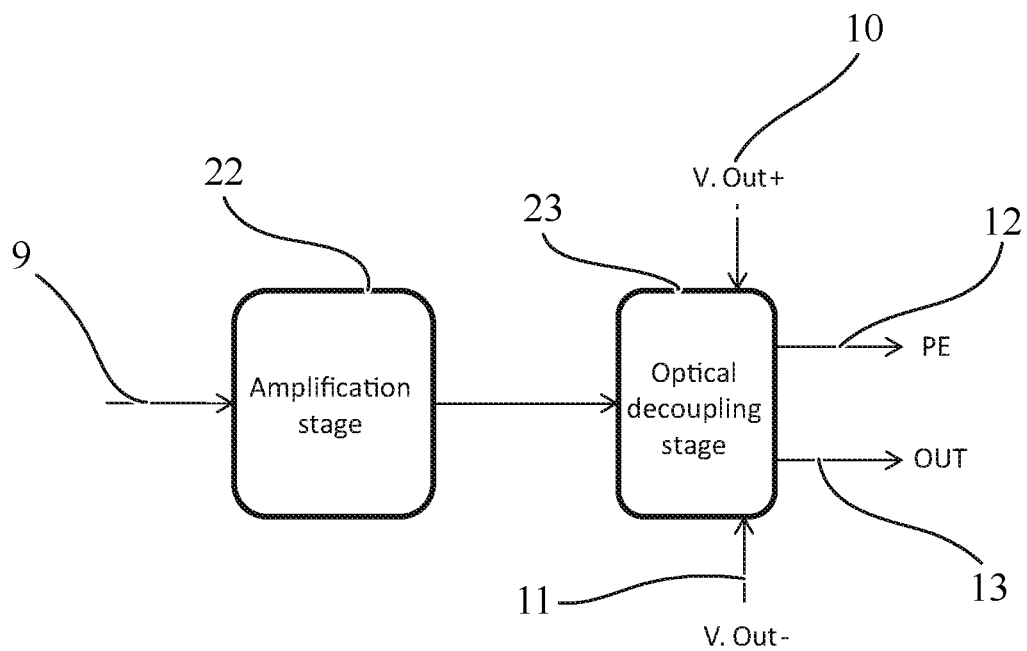
FIG. 8 shows a diagram for the decoupled output stage circuit (4), consisting of an amplification stage circuit (22) connected to an optical decoupling stage circuit (23), in an embodiment of the invention.

Referring to FIG. 8, the signal (9) is commanded by the control unit (1), typically, this signal (9) is a pulse train, where the amplitude, frequency, or pulse step (i.e. how wide the pulse is) are varied. Different results are obtained by changing these features of the signal (9).

The signal (9) comes from a control unit (1), which is a micro-controller, a computer, or a signal generator. Impulsive signals have low power, therefore, in order to deliver it at a greater load, it should be conditioned with an amplification stage circuit (22).

The signal (9) provided by a control unit (1) enter an amplification stage circuit (22). The output of said amplification stage (22), for security, does not connect transducers directly to the desired tissue. Thus, a decoupling circuit becomes necessary. The decoupling circuit allows for capacitive decoupling, decoupling by transformer, or as shown in FIG. 8, an optical decoupling stage circuit (23) in an embodiment of the invention.

The output of the amplification stage circuit (22), the positive V. Out (10) output and the negative V. Out (11) output of the source distributor circuit are connected to the optical decoupling stage circuit (23), from the multi-source distribution circuit (3). At the outputs of the optical decoupling circuit (23), PE (12) and Out (13), the impedance (i.e. the desired tissue) is connected through a transducer. PE (12) and Out (13) outputs are the outputs of the decoupled output stage circuit (4).

When the impulsive signal (9) enters the optical decoupling stage circuit (23), it switches to the frequency of the impulsive signal (9) sent by the control unit (1) and with the amplitude sent by the control unit (1).

Figure 9:
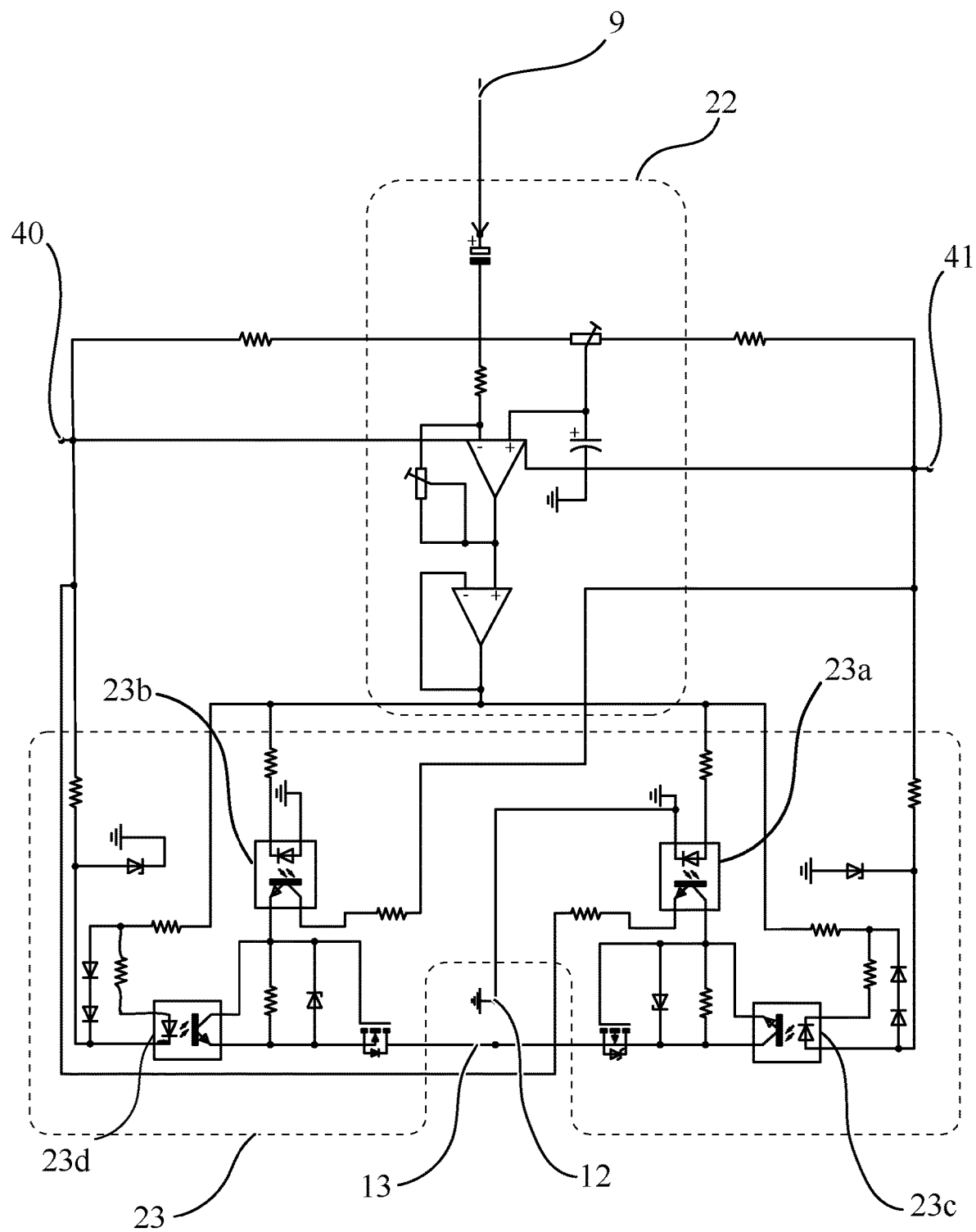
FIG. 9 shows the decoupled output stage circuit (4), consisting of an amplification stage (22), based on operational amplifiers, which is connected to an optical decoupling stage circuit (23), based on optocouplers, in an embodiment of the invention.

In an embodiment of the invention and referring to FIG. 9, the signal (9), commanded by the control unit (1), is connected to an amplification stage circuit (22). The amplification stage circuit (22) consists of an instrumentation amplifier, which is in turn made up of two operational amplifiers, where the first operational amplifier works as an inverting amplifier, and the second operational amplifier has the function of decoupling impedances.

The output of the amplification stage circuit (22) is connected to an optical decoupling stage circuit (23). The optical decoupling stage circuit (23) consists of a pair of optocouplers for the positive input source (41), which are arranged at the output of the amplification stage circuit (22), with their respective resistive impedance.

One of these optocouplers, specifically optocoupler (23c), protects the circuit segment for the negative external source (40) when the impulsive signal (9) switches the positive external source (41). Moreover, the second optocoupler integrated circuit (34a) is switched to connect the positive external source (41) to the segment of the circuit having a Zener diode, a resistive impedance and a MOSFET transistor, in order to condition the output signal. This output signal is sent through the PE (12) and Out (13) outputs.

The optical decoupling stage circuit (23) also has a pair of optocouplers for the negative input source (40), which are arranged at the output of the amplification stage circuit (22), with their respective resistive impedance.

One of these optocouplers, specifically optocoupler (23d), protects the circuit segment for the positive external source (41) when the impulsive signal (9) switches the negative external source (40). Moreover, the first optocoupler integrated circuit (16a) is switched to connect the negative external source (40) to the segment of the circuit having a Zener diode, a resistive impedance and a MOSFET transistor, in order to condition the output signal. This output signal is sent through the PE (12) and Out (13) outputs.

PE (12) and Out (13) outputs are connected at the output of the optical decoupling stage (23), where transducers are directly connected.

Transducers receive the positive V. Out (10) and negative V. Out (11) signals, modulated by the signal amplified by the amplification stage circuit (22). Depending upon the type of transducer, the requirement of the input source changes, therefore, it is necessary to change the load connected to the multi-source distribution circuit (3).

Figure 10:
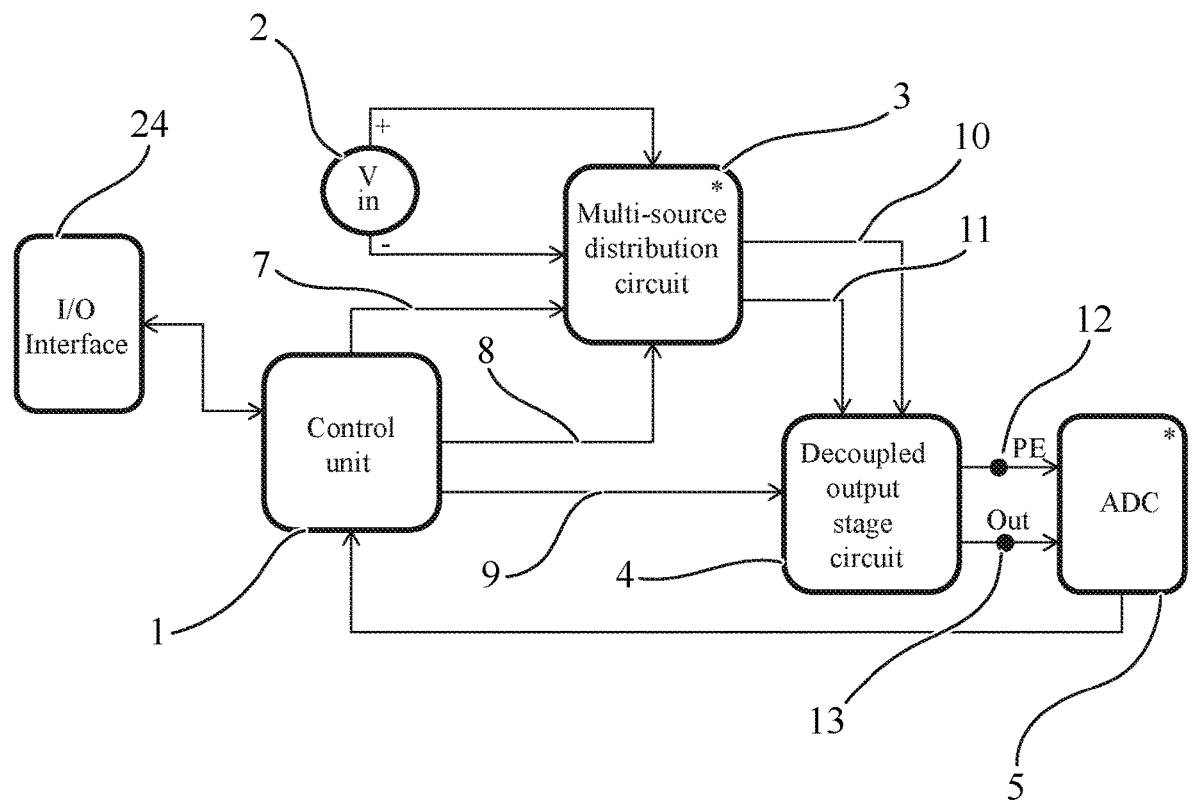
FIG. 10 shows a diagram of the invention where and input/output I/O interface (24) is connected to the control unit (1), which allows the user to interact with the device.

Referring to FIG. 10; the control unit (1) has a user interface or I/O input and output interface (24), which is a computing device with a display screen, an LCD, a monitor to display feedback (14) being delivered by the analog-to-digital converter [ADC] (5) to the control unit (1), in order to observe the behavior of the impedance connected at PE (12) and Out (13) spots of the decoupled output stage circuit (4).

The user interface or I/O input and output interface (24) allows an expert user to send orders to the control unit (1) to change the features of the signal (9) that the control unit (1) must send to the decoupled output stage circuit (4).

The control unit (1) is in turn connected to the multi-source distribution circuit (3) to send orders on which input source is to be used. The distributor circuit is connected to a dual positive/negative external source (2). Outputs of the multi-source distribution circuit (3)—positive V. Out (10) and negative V. Out (11)—are connected to the decoupled output stage circuit (4). Outputs of the decoupled output stage circuit (4)—PE (12) and Out (13)—are connected to an analog-to-digital converter [ADC] (5), which sends a feedback signal (14) to the control unit (1).

Figure 11:
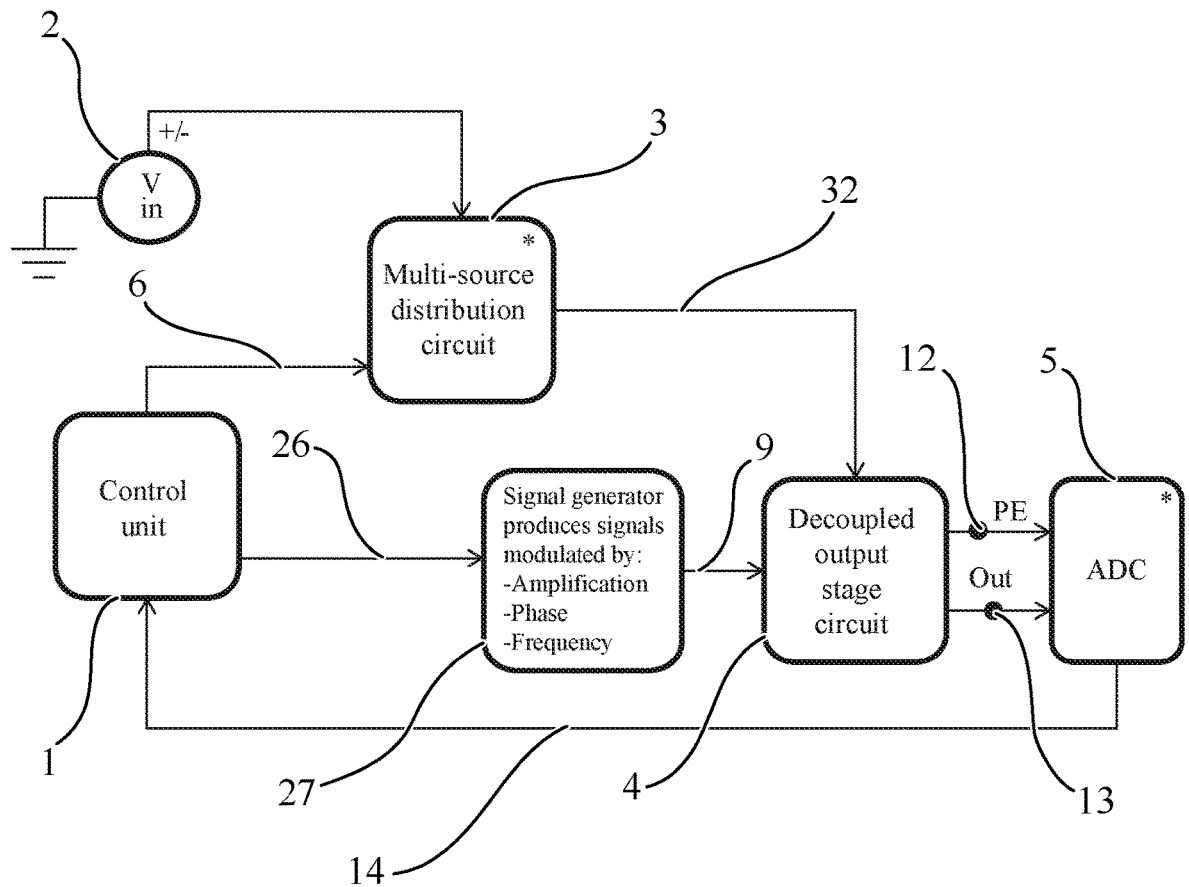
FIG. 11 shows a diagram of the invention where a signal generator (27) is connected to the control unit (1) and the decoupled output stage circuit (4), in an embodiment of the invention.

Referring to FIG. 11, the multi-source distribution circuit (3) is connected to an external source (2) that is positive or negative, and to the control unit (1) through a source control line (6). The control unit (1) is connected to a signal generator (27), through a signal control line (26). The signal generator (27) sends the signal (9) to the decoupled output stage circuit (4). The decoupled output stage circuit (4) receives the signal (9) sent by the signal generator (27) and the V. Out (32) signal sent by the multi-source distribution circuit (3).

Outputs of the decoupled output stage circuit (4)—PE (12) and Out (13)—are connected to an analog-to-digital converter [ADC] (5), which sends a feedback signal (14) to the control unit (1) for monitoring the behavior of the impedance connected to PE (12) and Out (13).

Figure 12:
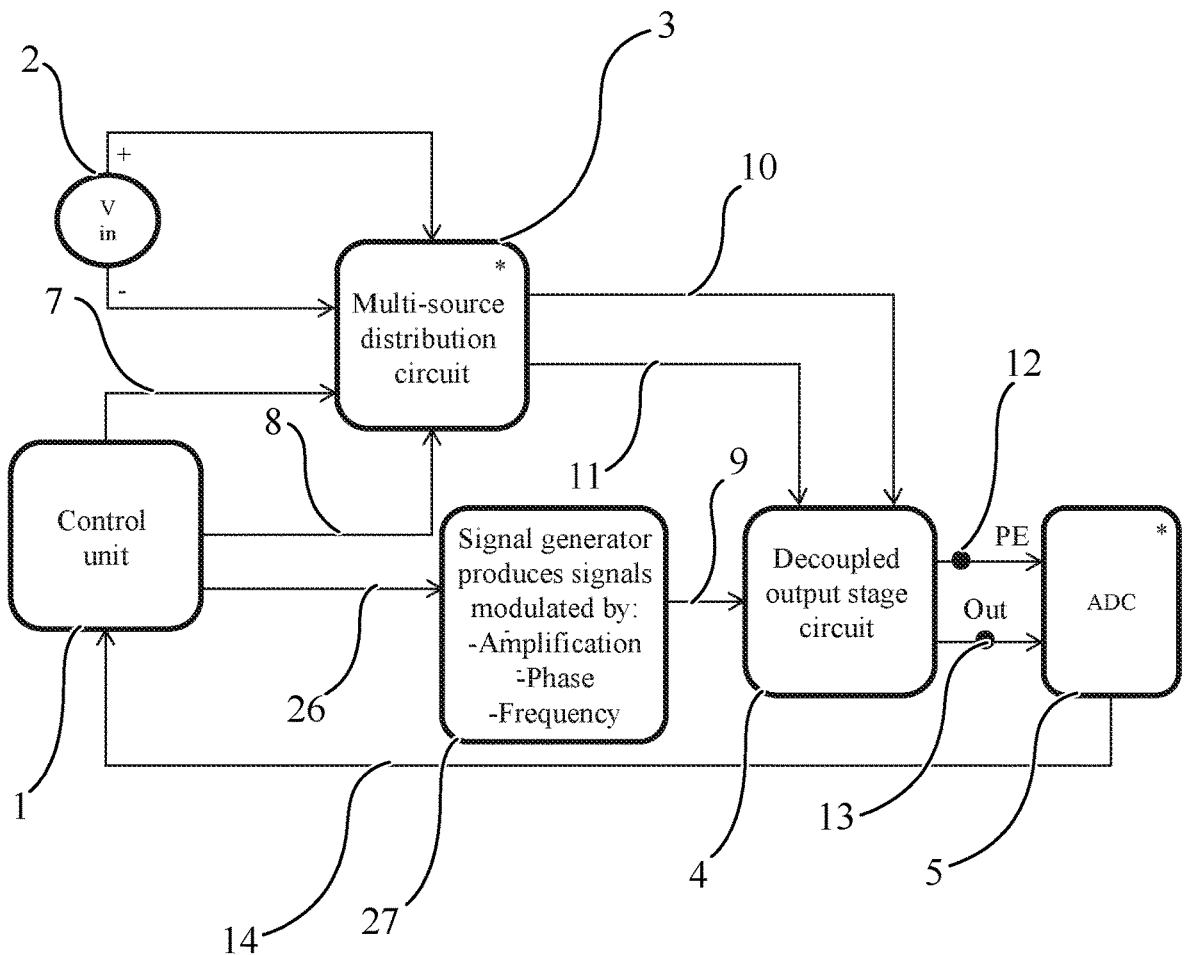
FIG. 12 shows a diagram of the invention where the external source (2) us a dual source and a signal generator (27) is connected to the control unit (1) and the decoupled output stage circuit (4), in an embodiment of the invention.

Referring to FIG. 12, the multi-source distribution circuit (3) is connected to a dual positive/negative external source (2) and to the control unit (1) through the high source control line (7) and the low source control line (8). The control unit (1) is connected to a signal generator (27), through a signal control line (26). The signal generator (27) sends the signal (9) to the decoupled output stage circuit (4), which in turn receives the positive V. Out (10) signal and the negative V. Out (11) signal sent by the multi-source distribution circuit (3).

Outputs of the decoupled output stage circuit (4)—PE (12) and Out (13)—are connected to an analog-to-digital converter [ADC] (5), which sends a feedback signal (14) to the control unit (1) for monitoring the behavior of the impedance connected to PE (12) and Out (13) channels.

Figure 13:
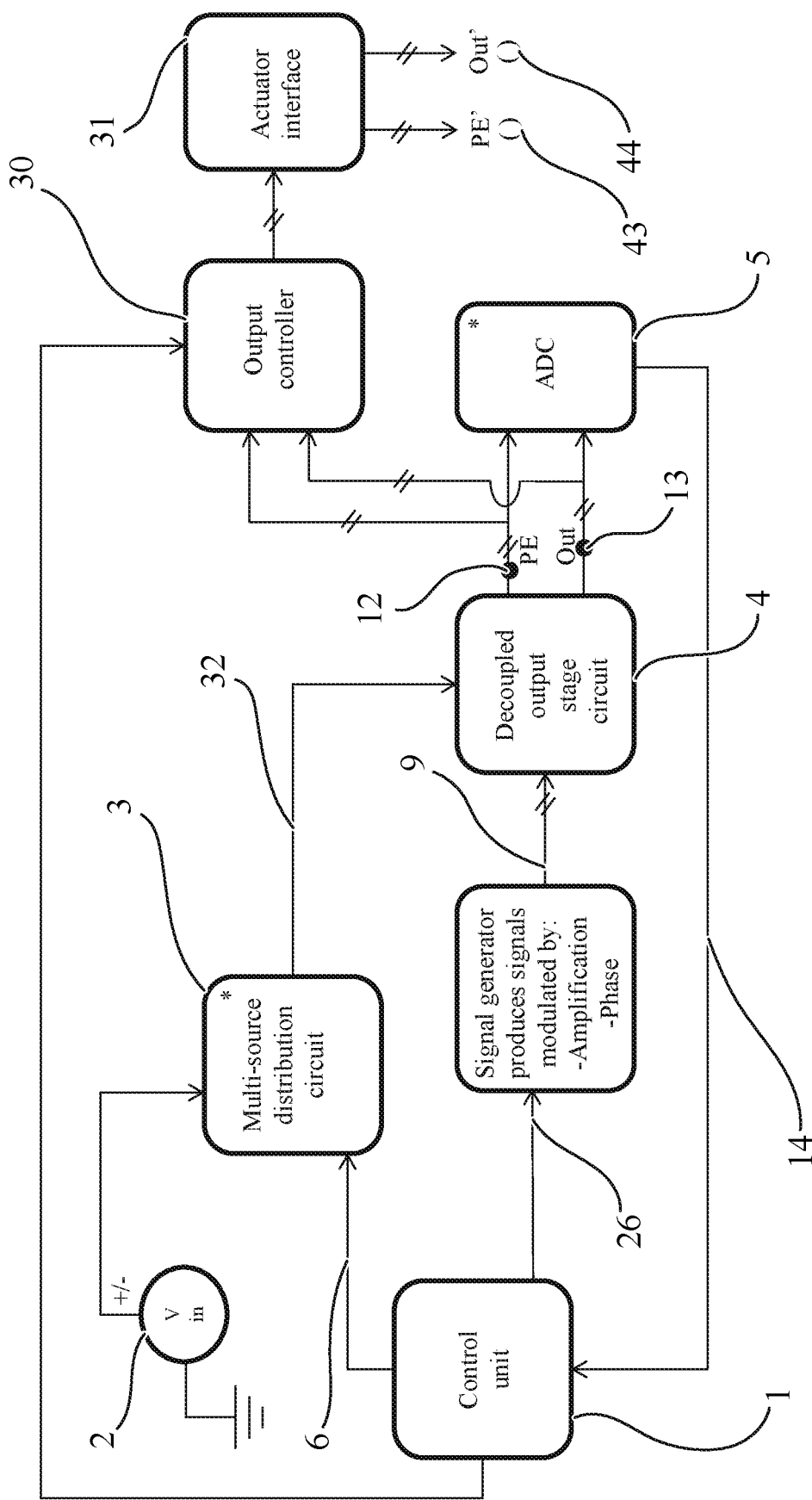
FIG. 13 shows a diagram of the invention where the control unit (1) is connected to an output controlling circuit (30), which is connected to an actuator interface (31), in an embodiment of the invention.

Referring to FIG. 13, the multi-source distribution circuit (3) is connected to an external source (2) that is positive or negative, and to a control unit (1) through a source control line (6). The control unit (1) is connected to a signal generator (27). The signal generator (27) sends two or more signals (9) to two or more decoupled output stage circuits (4).

The signal (9) sent by the signal generator (27) and the V. Out signal (32) sent by the multi-source distribution circuit (3) enter the decoupled output stage circuits (4). Each output stage circuit is connected through the PE (12) and Out (13) outputs to an analog-to-digital converter [ADC] (5), which sends a feedback signal (14) to the control unit (1), for monitoring.

All PE (12) and Out (13) outputs of each decoupled output stage circuit (4) are connected to an output controlling circuit (30). The output controlling circuit (30) receives a signal commanded by the control unit (1), which allows to choose which transducer is to be stimulated. An actuator interface (31) is connected at the output of the output controlling circuit (30). Two or more transducers are connected to the actuator interface (31), through the PE' (43) and Out' (44) outputs.

Figure 14:
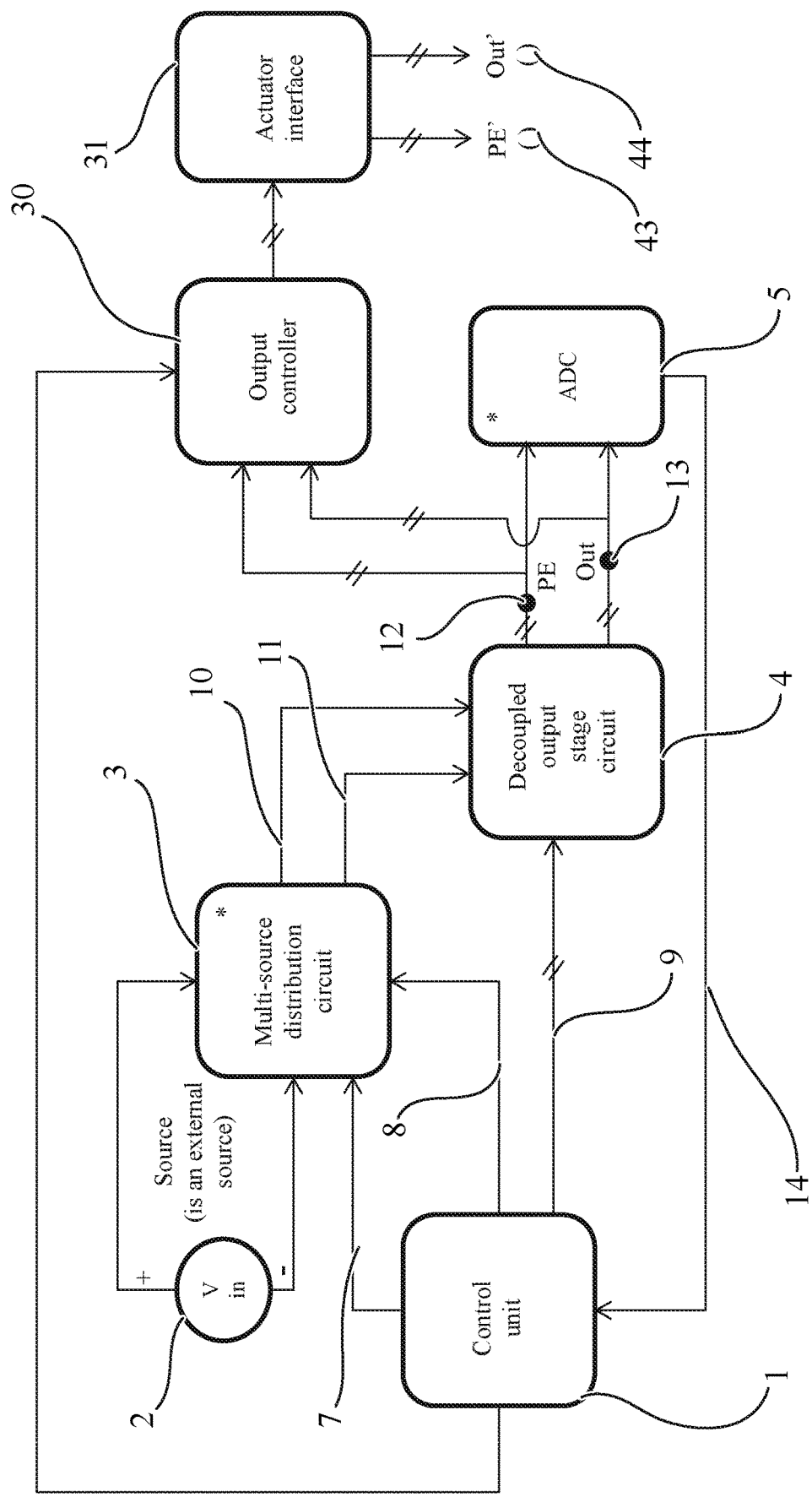
FIG. 14 shows a diagram of the invention where the control unit (1) is connected to an output controlling circuit (30), which is connected to an actuator interface (31), in an embodiment of the invention. In addition, the external source (2) is a dual source.

Referring to FIG. 14, the multi-source distribution circuit (3) is connected to a dual positive/negative external source (2) and to a control unit (1) through a high source control line (7) and a low source control line (8), which allows to switch between positive source and negative source. The control unit (1) sends two or more signals (9) to two or more decoupled output stage circuits (4).

The signal (9) sent by the control unit (1), the positive V. Out signal (10) and the negative V. Out signal (11) sent by the multi-source distribution circuit (3) enter the uncoupled output stage circuits (4). Each output stage circuit is connected through the PE (12) and Out (13) outputs to an analog-to-digital converter [ADC] (5), which sends a feedback signal (14) to the control unit (1), for monitoring.

All PE (12) and Out (13) outputs of each decoupled output stage circuit (4) are connected to an output controlling circuit (30). The output controlling circuit (30) receives a signal commanded by the control unit (1), which allows to choose which transducer is to be stimulated. An actuator interface (31) is connected at the output of the output controlling circuit (30). Two or more transducers are connected to the actuator interface (31), through the PE'(43) and Out' (44) outputs.

Figure 15:
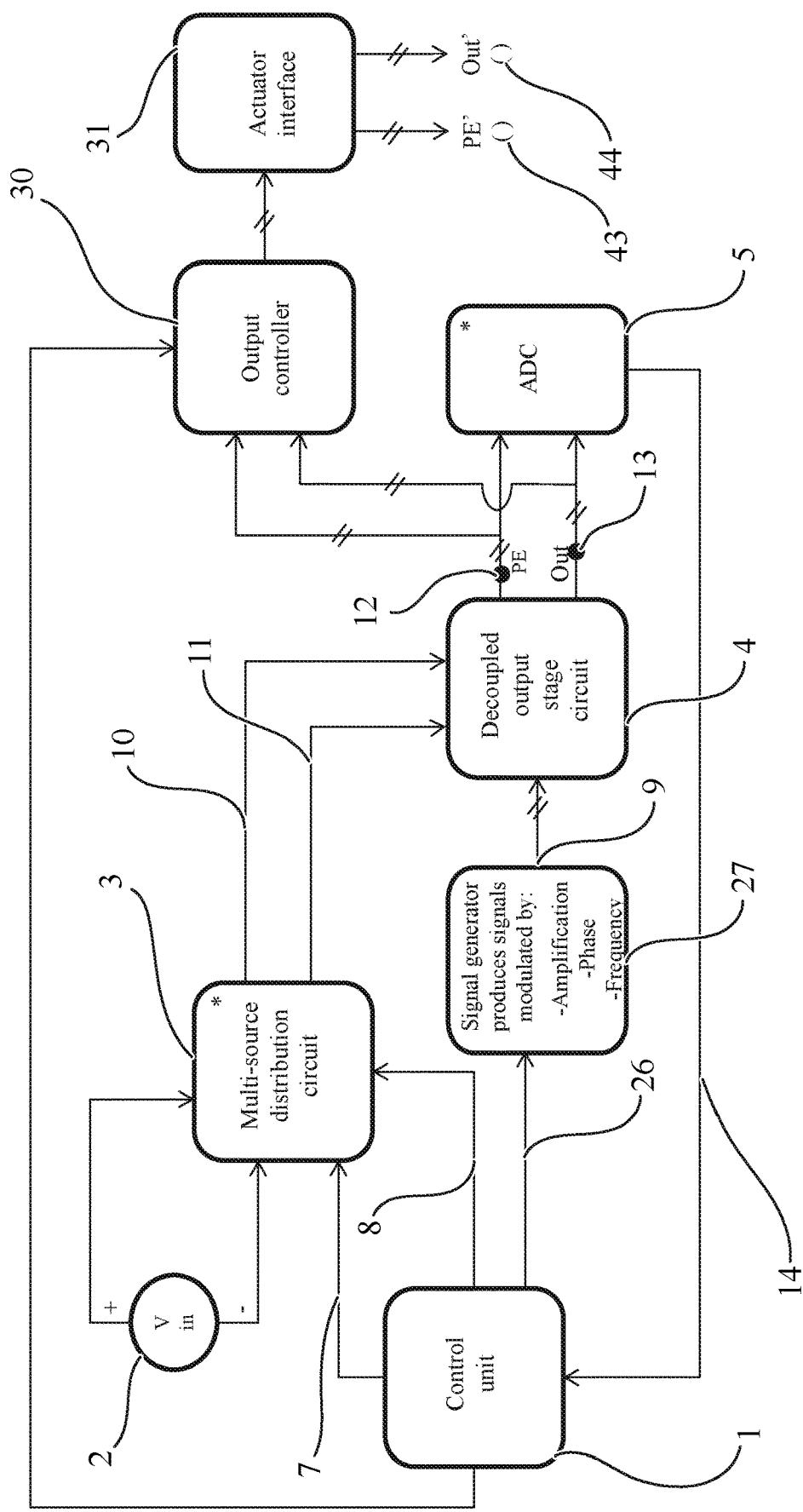
FIG. 15 shows a diagram of the invention where the control unit (1) is connected to an output controlling circuit (30) and to a signal generator (27); the output controlling circuit (30) is connected to an actuator interface (31), in an embodiment of the invention.

Referring to FIG. 15, the multi-source distribution circuit (3) is connected to a dual positive/negative external source (2) and to a control unit (1) through a high source control line (7) and a low source control line (8), which allows to switch between positive source and negative source. The control unit (1) is connected to a signal generator (27). The signal generator (27) sends two or more signals.

The signal (9) sent by the signal generator (27), the positive V. Out signal (10) and the negative V. Out signal (11) sent by the multi-source distribution circuit (3) enter the uncoupled output stage circuits (4). Each output stage circuit is connected through the PE (12) and Out (13) outputs to an analog-to-digital converter [ADC] (5), which enables feedback (14) to the control unit (1), for monitoring.

All PE (12) and Out (13) outputs of each decoupled output stage circuit (4) are connected to an output controlling circuit (30). The output controlling circuit (30) receives a signal commanded by the control unit (1), which allows to choose which transducer is to be stimulated. An actuator interface (31) is connected at the output of the output controlling circuit (30). Two or more transducers are connected to the actuator interface (31), through the PE'(43) and Out' (44) outputs.

Figure 16:
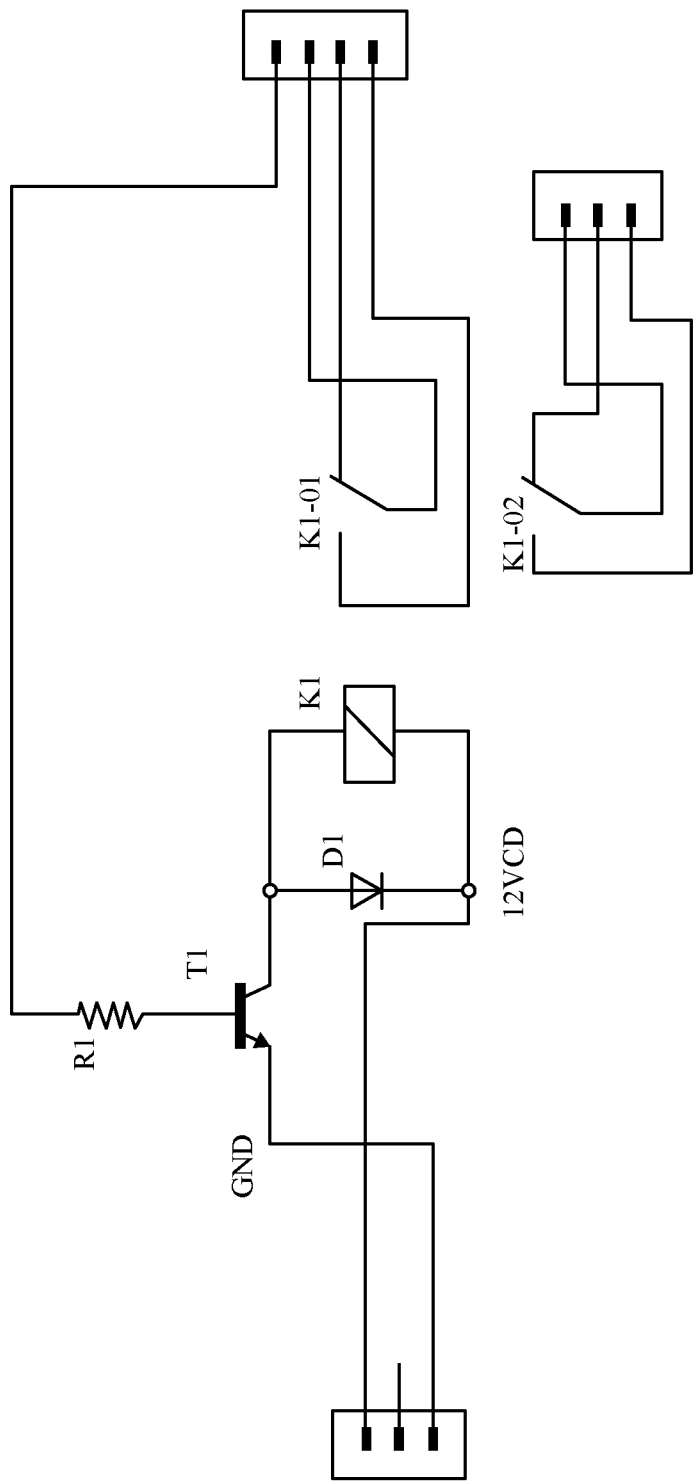
FIG. 16 shows a relay circuit, consisting of a transistor connected to a relay, with control using switches.

Referring to FIG. 16, it shows an example of relay circuit. Relay circuit consists of a pair of switches that allow to select whether a transistor starts to conduct or not. When the transistor starts to conduct allows the relay coil to be connected to GND, thus changing the relays state.

Figure 17:
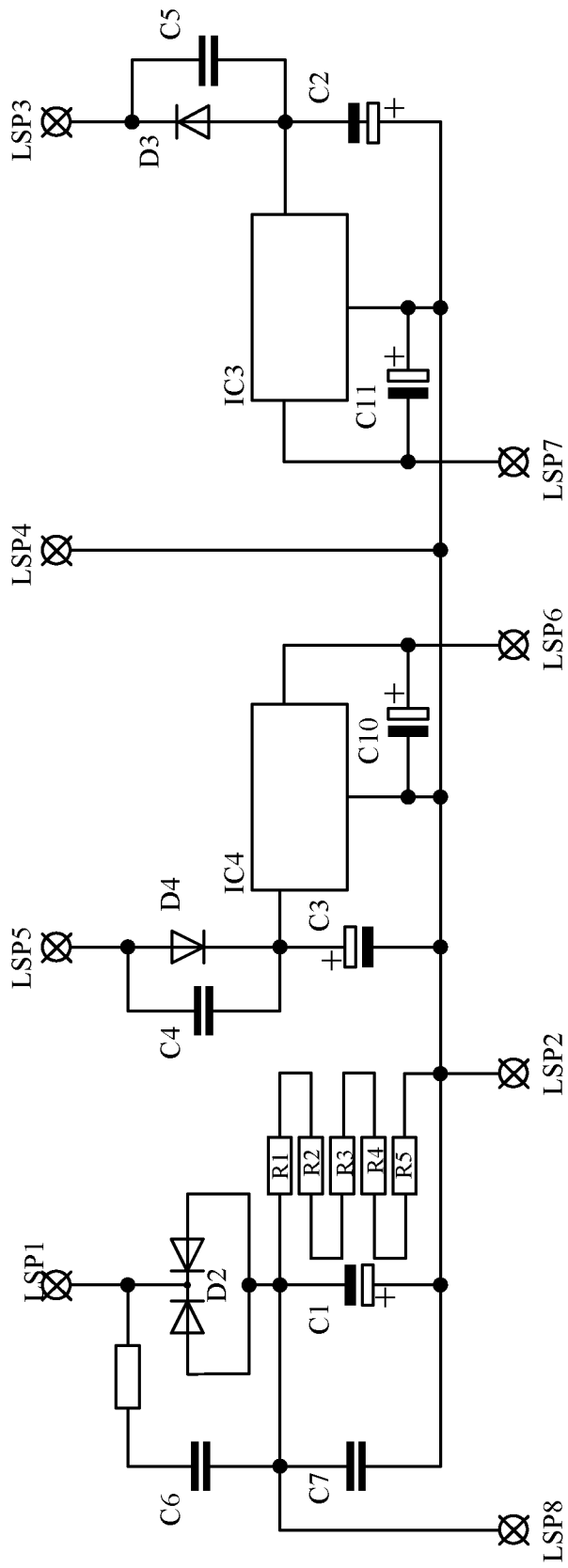
FIG. 17 shows a circuit for an external source (2), consisting of a rectification stage connected to a regulation stage.

Referring to FIG. 17, it shows a circuit for a dual source of 12 volts and −12 volts. This circuit consists of a rectifier, filter and regulators of 12 volts and −12 volts. The segment of the rectification circuit comprises two diodes, a group of resistances and capacitors. After the rectification stage are two stages, which depend upon the voltage; if it is positive, it goes through a voltage regulator of 12 Volts. If the rectified voltage is negative, it goes through a voltage regulator of −12 Volts.

In a non-illustrated embodiment of the invention, the multi-source distribution circuit comprises a control unit (1) connected to a source output selector (20). A voltage regulator circuit (18) is connected to a current limiter (19). The current limiter (19) is connected to a capacitor (21), to a capacitor bank (33) and to the source output selector (20), wherein the control unit (1) controls the source output selector (20) by means of an output control signal bus (15), the source output selector (20) connects or disconnects one or more capacitors from the capacitor bank (33).

Optionally, in the multi-source distribution circuit, the control unit (1) is connected to a controlled switch circuit (16). The controlled switch circuit (16) is connected to the voltage regulator circuit (18) and to an impedance (17), which is connected to the voltage regulator circuit (18) and to the controlled switch circuit (16). Wherein the control unit (1) controls the controlled switch circuit (16) by means of a source control signal (6).

Alternatively, in the multi-source distribution circuit, the control unit (1) is connected to a second controlled switch circuit (34) connected to a second voltage regulator circuit (36) and to a second impedance (35); the second impedance (35) connected to the second voltage regulator circuit (36) and the second controlled switch circuit (34), the second voltage regulator circuit (36) is connected to a second current limiter (37), which is connected to a second capacitor (38), a second capacitor bank (39) and the source output selector (42); wherein the control unit (1) controls the opening and closing of the second controlled switch circuit (34) through the source control signal (6) and controls the second source output selector (42) through the output control signal (15).

Also, in an embodiment of this invention, for example, the multi-source distribution circuit, the control unit (1) is connected to a third source output selector (63) connected to the first current limiter (19) and to the first voltage regulator (18). A fourth source output selector (64) connected to the second current limiter (37) and to the second voltage regulator (36).

Also, in an embodiment of this invention, for example, the multi-source distribution circuit, the computing unit (1) is connected to a third source output selector (63) connected to the first current limiter (19) and to the first voltage regulator (18). A fourth source output selector (64) connected to the second current limiter (37) and to the second voltage regulator (36).

It should be understood that this invention is not limited to the described and illustrated embodiments, and the person trained on the technique will understand that numerous variations and modifications can be made that do not depart from the spirit of the invention, which is only defined by the following claims.

The invention claimed is:

1. An electrical and magnetic tissue stimulation device comprising:
  a multi-source distribution circuit comprising:
    a first source output selector;
    a first voltage regulator circuit;
    a first current limiter;
    a first capacitor;
    a first V. Out output;
    a first capacitor bank comprising a first plurality of switchable capacitors connected through the first source output selector,
    wherein said first voltage regulator circuit is connected to said first current limiter; and
    wherein said first current limiter is connected to:
      said first capacitor;
      the first source output selector; and
      said first capacitor bank; and
  a control unit; and
  a decoupled output stage circuit with a first output and a second output connected to the multi-source distribution circuit and to said control unit;
  wherein the control unit:
    (i) is connected to and is configured to control the first source output selector by means of an output control signal through an output control signal bus, wherein the first source output selector is configured to connect or disconnect one or more of the first plurality of switchable capacitors from the first capacitor bank, and wherein when one or more of the first plurality of switchable capacitors from the first capacitor bank is connected or disconnected, said V. Out output load changes, and
    (ii) is configured to generate the first output and the second output to electrically and magnetically stimulate a tissue.

2. The device of claim 1, further comprising a transducer, wherein the decoupled output stage circuit is connected to the transducer.

3. The device of claim 1, further comprising an analog to digital converter (ADC), wherein the decoupled output stage circuit and the control unit are connected to the ADC.

4. The device of claim 1, wherein the multi-source distribution circuit is dual source.

5. The device of claim 1, wherein the multi-source distribution circuit further comprises:
  a first controlled switch circuit; and
  a first impedance;
  wherein said first controlled switch circuit is connected to said control unit, to said first voltage regulator circuit and to said first impedance; and
  said first impedance is connected to the first voltage regulator circuit,
  wherein the control unit controls the first controlled switch circuit by means of a source control signal.

6. The device of claim 5, wherein the multi-source distribution circuit further comprises:
  a second controlled switch circuit connected to a second voltage regulator circuit and to a second impedance;
  the second impedance connected to the second voltage regulator circuit and to the second controlled switch circuit;
  the second voltage regulator circuit connected to a second current limiter; and
  the second current limiter connected to a second capacitor, to a second capacitor bank and to a second source output selector;
  wherein the control unit controls the opening and closing of the second controlled switch circuit through the source control signal and controls the second source output selector through the output control signal.

7. The device of claim 6, wherein the multi-source distribution circuit further comprises:
a third source output selector connected to the first current limiter and to the first voltage regulator circuit; and
a fourth source output selector connected to the second current limiter and the second voltage regulator circuit;
the third source output selector and the fourth source output selector connected to the control unit.

8. The device of claim 5, further comprising an additional source output selector connected to the first capacitor bank.

9. The device of claim 1, further comprising an optical decoupling stage circuit, and wherein the decoupled output stage circuit comprises an amplification stage connected to the optical decoupling stage circuit.

10. The device of claim 1, further comprising an input/output (I/O) interface connected to the control unit.

11. The device of claim 1, wherein the control unit is connected to a signal generator, and the signal generator is connected to the decoupled output stage circuit.

12. The device of claim 1, wherein the control unit is connected to an output controller, the decoupled output stage circuit is connected to the output controller; and the output controller is connected to an actuator interface which generates a PE' and an Out' signals.

13. An electrical and magnetic tissue stimulation device comprising:
a multi-source distribution circuit comprising:
a first source output selector;
a second source output selector;
a positive voltage regulator circuit;
a negative voltage regulator circuit;
a positive current limiting circuit;
a negative current limiting circuit;
a first capacitor;
a second capacitor;
a first V. Out output;
a first capacitor bank comprising a first plurality of switchable capacitors connected through the first source output selector,
a second capacitor bank comprising a second plurality of switchable capacitors connected through the second source output selector,
wherein said positive voltage regulator circuit is connected to said positive current limiting circuit,
wherein said negative voltage regulator circuit is connected to said negative current limiting circuit;
a first controlled switch circuit connected to a high source control signal, wherein a first high protection impedance, a second high protection impedance, the positive voltage regulator circuit, and the positive current limiting circuit are connected to an output of the first controlled switch circuit;
the positive current limiting circuit connected to the first capacitor;
the first capacitor connected to the first source output selector and to the first capacitor bank;
a second controlled switch circuit connected to a low source control signal, wherein a first low protection impedance, a second low protection impedance, the negative voltage regulator circuit, and the negative current limiting circuit are connected to an output of the second controlled switch circuit;
the negative current limiting circuit connected to the second capacitor; and
the second capacitor connected to the second source output selector and to the second capacitor bank;
a control unit; and
a decoupled output stage circuit with a first output and a second output connected to the multi-source distribution circuit and to said control unit;
wherein the control unit:
(i) is connected to and is configured to control the first source output selector by means of an output control signal through an output control signal bus, wherein the first source output selector is configured to connect or disconnect one or more of the first plurality of switchable capacitors from the first capacitor bank, and wherein when one or more of the first plurality of switchable capacitors from the first capacitor bank is connected or disconnected, said V. Out output load changes, and
(ii) is configured to generate the first output and the second output to electrically and magnetically stimulate a tissue.

14. A system for electrical and magnetic tissue stimulation comprising:
a multi-source distribution circuit comprising:
a first source output selector;
a first voltage regulator circuit;
a first current limiter;
a first capacitor;
a first V. Out output;
a first capacitor bank comprising a first plurality of switchable capacitors connected through the first source output selector;
wherein said first voltage regulator circuit is connected to said first current limiter, and said first current limiter is connected to:
said first capacitor;
to said first capacitor bank; and
the first source output selector; and
a control unit connected to and configured to control the first source output selector by means of an output control signal through an output control signal bus, wherein the first source output selector is configured to connect or disconnect one or more of the first plurality of capacitors from the first capacitor bank, wherein when one or more capacitors of the first plurality of capacitors from the first capacitor bank is connected or disconnected, said V. Out output load changes.

15. The system claim 14, wherein the multi-source distribution circuit further comprises a first controlled switch circuit, wherein the control unit is connected to the first controlled switch circuit, the first controlled switch circuit connected to the first voltage regulator circuit and to a first impedance, the first impedance is connected to the first voltage regulator circuit and to the first controlled switch circuit wherein the control unit controls the first controlled switch circuit by means of a source control signal.

16. The system of claim 15, wherein the multi-source distribution circuit further comprises a second controlled switch circuit, wherein the control unit is connected to the second controlled switch circuit, the second controlled switch circuit is connected to a second voltage regulator circuit and to a second impedance;
the second impedance is connected to the second voltage regulator circuit and to the second controlled switch circuit;
the second voltage regulator circuit is connected to a second current limiter; and the second current limiter is connected to a second capacitor, to a second capacitor bank and to a second source output selector;

wherein the control unit controls the opening and closing of the second controlled switch circuit through the source control signal and controls the second source output selector through the output control signal.

17. The system of claim 16, wherein the control unit is connected to:
a third source output selector connected to the first current limiter and to the first voltage regulator; and
a fourth source output selector connected to the second current limiter and to the second voltage regulator.

18. The system of claim 14, further comprising an additional source output selector connected to the first capacitor bank.

19. The system of claim 14, wherein the control unit is connected to an output controller, the decoupled output stage circuit is connected to the output controller; and the output controller is connected to an actuator interface which generates a PE' signal and an Out' signal.

20. The system of claim 14, wherein the control unit is configured to generate a first output and a second output to electrically and magnetically stimulate a tissue.

* * * * *